(12) United States Patent
Bloom

(10) Patent No.: US 7,582,777 B2
(45) Date of Patent: Sep. 1, 2009

(54) LONG CHAIN (C22-C50) POLYUNSATURATED HYDROCARBONS, DERIVATIVES, SYNTHESIS AND USES THEREOF

(75) Inventor: Paul D. Bloom, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 545 days.

(21) Appl. No.: 11/250,622

(22) Filed: Oct. 17, 2005

(65) Prior Publication Data

US 2006/0149085 A1 Jul. 6, 2006

Related U.S. Application Data

(60) Provisional application No. 60/618,796, filed on Oct. 15, 2004.

(51) Int. Cl.
| | | |
|---|---|---|
| C07D 303/04 | (2006.01) | |
| C07D 319/10 | (2006.01) | |
| C07D 407/06 | (2006.01) | |
| C07D 407/14 | (2006.01) | |
| C07C 1/20 | (2006.01) | |

(52) U.S. Cl. ............... 549/274; 549/512; 585/600; 585/606; 585/607; 205/462

(58) Field of Classification Search ............... 585/600, 585/606, 607; 205/462; 549/274, 512
See application file for complete search history.

(56) References Cited

U.S. PATENT DOCUMENTS

| 3,210,325 | A | | 10/1965 | De Witt et al. |
|---|---|---|---|---|
| 4,018,844 | A | * | 4/1977 | Meresz et al. ............... 585/16 |
| 5,719,301 | A | | 2/1998 | Sleeter |
| 6,696,581 | B1 | | 2/2004 | Sleeter |
| 2005/0234121 | A1 | | 10/2005 | Binder et al. |
| 2005/0245405 | A1 | | 11/2005 | Geier et al. |
| 2006/0020062 | A1 | | 1/2006 | Bloom |

FOREIGN PATENT DOCUMENTS

| GB | 394 073 | 6/1933 |
|---|---|---|
| WO | WO 2005/095378 | 10/2005 |
| WO | WO 2005/100519 | 10/2005 |
| WO | WO 2006/014483 | 2/2006 |

OTHER PUBLICATIONS

Weedon, Advances in Organic Chemistry:Methods and Results, New York, p. 1-34 (1960).*

Fox, F.L., "I. General.; II. Composition; III. Extraction and Refining of Oils; IV. Oil Testing Methods and Oil Properties; V. Classification and Use of Oils; VI. Processed and Chemically Modified Oils; VII. Kinds of Oils and Their Uses; Appendix," in: *Oils for Organic Coatings, Federation Series on Coatings Technology, Unit Three*, Federation of Societies for Paint Technology, Philadelphia, PA, pp. 1-47 (1965).

Furniss, B.S. et al. eds., "2.17.6. Electrolytic (Anodic) Synthesis (The Kolbe Reaction); 5.11.5. Electrolytic (Anodic) Coupling," *Vogel's Practical Organic Chemistry*, Fifth Ed., John Wiley and Sons, Inc., New York, pp. 115, 116, and 687-680 (1989).

Furniss, B.S. et al. eds., *Vogel's Practical Organic Chemistry*, Fifth Ed., John Wiley and Sons, Inc., New York, p. 484 (1989).

Klaas, M.R. and Warwel, S., "Chapter 10. New Oxidation Methods for Unsaturated Fatty Acids, Esters, and Triglycerides," in: *Recent Developments in the Synthesis of Fatty Acid Derivatives*, Knothe, G. and Derksen, J.T.P., eds., AOCS Press, Champaign, IL, pp. 157-181 (1999).

Ofedie, H.A., "Electrochemical Oxidation of Fatty Acids and Ethyl Lactate," *Powerpoint Presentation*, presented at Illinois State University, 32 pages (Oct. 15, 2004).

Ofedie, H.A., "Electrochemical Oxidation of Fatty Acids and Ethyl Lactate," *Thesis*, 69 pages, shelved Oct. 26, 2005 at The Milner Library of Illinois State University, and presented at Illinois State University (Dec. 9, 2004).

Schafer, H.J., "Recent Synthetic Applications of the Kolbe Electrolysis," *Chem. Physics Lipids* 24:321-333, Elsevier/North-Holland Scientific Publishers Ltd.(1979).

Weiper-Idelmann, et al., "Electroorganic Synthesis 65. Anodic Homocoupling of Carboxylic Acids Derived from Fatty Acids," *Acta Chem. Scan.* 52:672-682, Munksgaard International Publishers (1998).

* cited by examiner

*Primary Examiner*—Bernard Dentz
(74) *Attorney, Agent, or Firm*—Sterne, Kessler, Goldstein & Fox P.L.L.C.

(57) ABSTRACT

The present invention is directed to unsaturated or derivatized long chain ($C_{22}$-$C_{50}$) polyunsaturated hydrocarbons and a method of preparing the long chain hydrocarbons via electrocoupling of $C_{12}$-$C_{26}$ fatty acids. It has been found that soapstock is an inexpensive source of starting materials for the present method. The present invention is also directed to compositions comprising the long chain polyunsaturated hydrocarbons, which can be used as reactive diluents and modifiers in latex, epoxy, alkyd and polymer compositions. In another aspect, the present invention is directed to derivitization or ozonolysis of the long chain polyunsaturated hydrocarbons. The present method is also useful for preparing $C_{12\text{-}26}$ alkyl esters and $C_{12\text{-}26}$ carbon chain compounds containing a terminal olefin.

8 Claims, No Drawings

LONG CHAIN (C22-C50) POLYUNSATURATED HYDROCARBONS, DERIVATIVES, SYNTHESIS AND USES THEREOF

CROSS REFERENCE TO RELATED APPLICATIONS

This application claims the benefit of U.S. Provisional Application No. 60/618,796, filed Oct. 15, 2004, the contents of which are entirely incorporated by reference herein.

BACKGROUND OF THE INVENTION

1. Field of the Invention

This invention relates to long chain polyunsaturated hydrocarbons, derivatives, and uses thereof, methods of preparing the long chain polyunsaturated hydrocarbons and compositions comprising the polyunsaturated long chain hydrocarbons. The present method is also useful for preparing $C_{12-26}$ alkyl esters and $C_{12-26}$ carbon chain compounds containing a terminal olefin.

2. Related Art

Hydrocarbons are generally derived from crude oils. When crude oil is cracked, the different components in the oil are distilled and separated. Many of the fractions produced from the cracking process contain long chain hydrocarbons. These chemicals are widely used in industry and are found in innumerable products. Because crude oil is a non-renewable resource, alternative sources of long chain hydrocarbons are desirable.

Vegetable and animal oils are a source of long chain hydrocarbons. Vegetable oil fatty acids contained in the oil have carbon chains up to about 26 carbons in length. Thus, these oils can be useful sources of long chain hydrocarbons. Fish oils are enriched in long chain polyunsaturated fatty acids. However, the hydrocarbons are in the form of fatty acids, fatty acid esters or other forms that are used in biological processes.

Hydrocarbon chains derived from fatty acid salts are known in the art. Electrocoupling of fatty acid residues produces hydrocarbon chains (Vogel, A. I., Experiment 5.11 Hexacosane, in *Vogel's Practical Organic Chemistry*, 5th Ed., Eds. Furniss, B. S. et al., John Wiley & Sons, Inc., NY., 1989, p. 484; Weiper-Idelmann, A., et al., *Acta Chemica Scandinavica*, 52, 1998, 672-682; Schafer, H. J., *Chemistry and Physics of Lipids*, 24, 1979, 321-333. Methods known in the art yield saturated chains that are relatively short in length. Electrocoupling of polyunsaturated long chain fatty acids from oils, specifically vegetable oils, to produce long chain hydrocarbons that can be further derivatized has not been utilized.

Soapstock is an inexpensive source of vegetable oil fatty acids. When glyceride oils, e.g., animal fats or vegetable oils, are refined to remove free fatty acids and other impurities by alkali refining, the aqueous alkaline solution which is separated from the bulk of the refined oil contains alkali soaps of fatty acids together with substantial quantities of free fatty acids, glycerides thereof, and various impurities including water-soluble phosphatides such as lecithin. Some of the free fatty acids, glycerides, and impurities ordinarily will be emulsified in the resulting aqueous mixture by the soaps and the phosphatide-type components. This aqueous mixture is commonly known as "soap stock". Alternate, less refined or recycled fatty acid feedstocks are available. These feedstocks include acidulated soap stock (acid oils), used grease from restaurants, and all other acylglyceride esters of fatty acids that contain high levels of free fatty acids (FFA).

BRIEF SUMMARY OF THE INVENTION

It has been found that long chain ($C_{22}$-$C_{50}$) polyunsaturated hydrocarbons can be prepared by electrocoupling of $C_{12}$-$C_{26}$ unsaturated fatty acids. It has also been found that soapstock is an inexpensive starting material for preparing the long chain polyunsaturated hydrocarbons. In one aspect, the present invention is directed to a compound of Formula I:

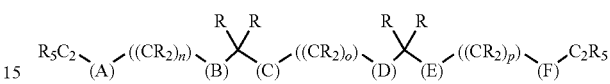

wherein, A, B, C, D, E and F can be one of the following structures:

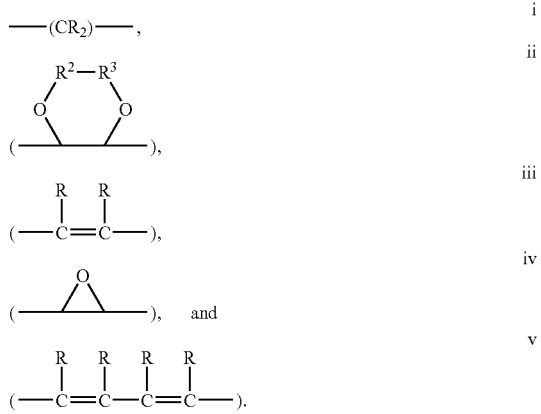

The present invention is also directed to methods of preparing a compound of Formula I. In another aspect, the present invention is directed to compositions comprising compounds of Formula I. Such compositions include, but are not limited to, coating compositions, thermoset plastics, polymer compositions and the like. The present method is also useful for preparing $C_{12-26}$ alkyl esters (disclosed herein as Formula II) and $C_{12-26}$ carbon chain compounds containing a terminal olefin (disclosed herein as Formula II). Compositions comprising compounds of Formula I or Formula II or mixtures thereof are also a subject of the present invention.

DETAILED DESCRIPTION OF THE INVENTION

In one aspect, the present invention is directed to a compound of Formula I:

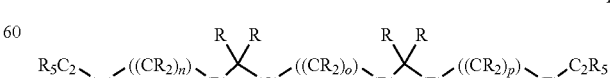

wherein, at least one of A, B, C, D, E and F is selected from the group consisting of:

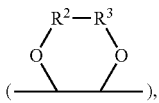

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl;

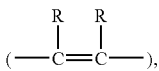

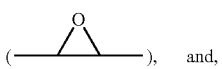 and, the other of A, B, C, D, E and F is independently selected from the group consisting of: i (shown above as —$(CR_2)$—, i, ii, iii, iv and v;

R is in each instance independently selected from the group consisting of:

hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl;

n is an integer between about 1 and about 6;
o is an integer between about 10 and about 20; and
p is an integer between about 1 and about 6,
provided that,
if C and D are both

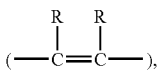

o is 14 or 22, and every instance of R is hydrogen, then at least one of A, B, E or F is other than $CH_2$.

When a compound of Formula I contains one or more double bonds as represented herein in each instance by the structure:

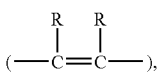

the double bond(s) in each instance can be either a cis or trans configuration. The structure used herein to identify the double bond is not intended to show stereochemistry. Specifically, the structure is not intended to represent solely a cis or trans configuration. Rather, where any double bond is identified by the above structure, the structure represents an optional cis and trans configuration in each instance.

Useful values of A, B, C, D, E, and F include those listed above. In all embodiments, at least one of A, B, C, D, E and F is other than i, i.e., —$(CR_2)$—. In more preferred embodiments, at least one of A, B, C, D, E and F is ii, iii, iv or v as depicted above. When at least one of A, B, C, D, E and F is ii, it is more preferable that the other of A, B, C, D, E and F is i, ii, or iii. When at least one of A, B, C, D, E and F is iii, it is more preferable that the other of A, B, C, D, E and F is iii, i, or ii.

Useful values of n include integers between about 1 and about 6. Preferably, n is 1, 2 or 3. The value of n is independent of the values for o and p. However, in certain preferred embodiments, a particular value of n is specified in combination with specific values of o and p.

Useful values of p include integers between about 1 and about 6. Preferably, p is 1, 2 or 3. The value of p is independent of the values for o and n. However, in certain preferred embodiments, a particular value of p is specified in combination with specific values of o and n.

Useful values of o include integers between about 10 and about 20. Preferably, o is between about 10 and about 16. Most preferably, o is about 14. The value of o is independent of the values for n and p. However, in certain preferred embodiments, a particular value of o is specified in combination with specific values of n and p.

Useful values of R include hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl. The carbon chain can be functionalized by methods well known in the art. The groups which can be added to functionalize the chain include long-chain substituents. For example, the chain can be functionalized with a chain of 26 carbons, such as hexacosanoic acid; C26:0 that can be derived from beeswax. As another example, substituent groups can contain a chain of 24 carbons, such as lignoceric acid; C24:0 that can be derived from groundnut oil.

Preferred chain lengths would be $C_2$-$C_{18}$ derived from carboxylic acids. Addition of functionality to the chain can be derived in a variety of methods. Friedel-Crafts acylation, allylic oxygenation, anodic acetoxylation, hydroformylation, ene-reactions, Diels-Alder reactions are all possible functionalization methods for modification of the chain in the present compounds. Most preferred substituents contain R groups that modify the compound's rheologic properties as discussed herein. Another preferred value of R is hydrogen. Each R is independently selected from all other occurrences of R on a particular molecule.

Electrocoupling of fatty acids containing conjugated double bonds can yield compounds of Formula I, II or III which contain at least one group represented by structure "v":

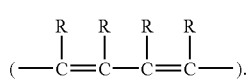

Such compounds are encompassed by the Formulae disclosed herein which contain "v." Of particular interest are compounds where the allylic positions are more reactive because of the conjugation. Further, electrocoupling of polyunsaturated long chain fatty acids that do not contain conjugated double bonds can yield compounds which isomerize to form conjugated double bonds. Such compounds are also encompassed by the Formulae disclosed herein which contain "v."

Thus, in conjugated compounds, at least one of A, B, C, D, E and F is represented as v. Preferably, only one of A, B, or C, and only one of D, E and F is v. Also preferred are compounds where only one of A, B, C, D, E and F is v. Compounds containing conjugated double bonds can also contain additional double bonds within the carbon chain that are not in conjugation with the double bonds represented by v.

As a preferred example, conjugated linoleic acid can be electrocoupled. Conjugated linoleic acid includes cis-9 and trans-11 double bonds, or, alternatively, trans-10 and cis-12 double bonds. Both fatty acid residues are isomers of linoleic acid. Electrocoupling (cross-coupling) of one residue of conjugated linoleic acid with a chemically different fatty acid residue would result in a structure of Formula I wherein A is i, n=1, B is i, and C is v. In this structure, values of D, E, F, o and p depend on the structure of the chemically different fatty acid residue. Electrocoupling of two residues of conjugated linoleic fatty acid would result in a structure of Formula I wherein A is i, n=1, B is i, C is v, o=14 to 16, D is v, E is i, p=1, and F is i.

Other preferred compounds include the following structures:

aliphatic amines (amino($C_{1-26}$)alkyl). Most preferably, the length of the chain is between about 1 and about 10 carbons. The addition of these aliphatic groups can disrupt chain packing to prevent crystallization.

In the above structures, 1-9, A, B, C, D, E and F are shown as —($CR_2$)— or

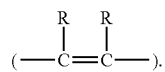

The double bonds in structures 1-9 can be derivatized to form oxirane or dioxanone ring systems.

When a compound of Formula I contains a dioxanone ring,

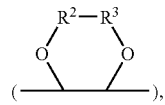

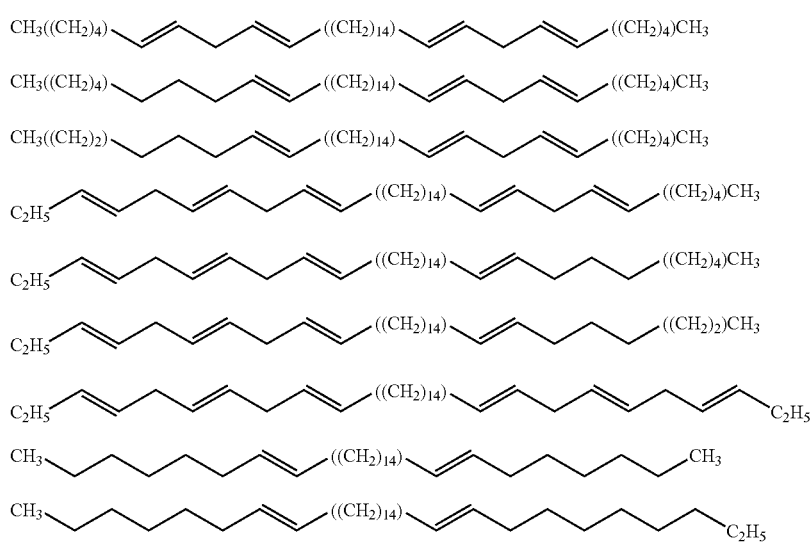

In the above structures, 1-9, R in each instance is shown as hydrogen. In other preferred compounds, each R can be independently selected from the group consisting of: hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl. Preferably, the carbons are derivatized to contain substituents that modify the chain's physical and chemical properties in its end use application. Such modifications include those that affect surfactant properties, pour point, viscosity, crystallization, polymerization and the like. Preferably, substituents added for the above purposes include esters, alcohols, amides, amines, ketones, epoxides, carboxylic acids, alkenes, alkynes, azides, hydrazides, imines, oximes, etc. More preferred substituents will be branched or straight chain $C_{1-26}$ alkyl chains, aliphatic alcohols (hydroxy($C_{1-26}$)alkyl), and embedded in the carbon chain via two adjacent carbons in the chain, the compound can be optionally substituted at the positions numbered $R^2$ and $R^3$. One of $R^2$ and $R^3$ is a carbonyl and the other of $R^2$ and $R^3$ is $CR^4R^5$, wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, heteroaryl, $C_{3-6}$ cycloalkyl and phenyl($C_{1-26}$)alkyl. Thus, there are two possible orientations of the ring relative to the chain. In one orientation, the carbonyl in the ring is on the carbon nearest the chain terminus. In the other orientation, the carbonyl is on the carbon nearest the axis of the chain, which may or may not be a symmetrical chain as shown in structures 1-9 above.

In the present invention, the carbon chain can have one or more oxirane rings depicted by the following structure iv:

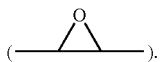

The oxirane ring is formed by adjacent carbons in the chain. Thus, the ring is embedded in the chain. Embedded oxirane rings can be formed by epoxidizing double bonds present in the chain. A carbon chain that has multiple sites of unsaturation can be epoxidized to a greater extent. However, not all double bonds of the chain must be epoxidized.

The present invention is also directed to methods of preparing a compound of Formula I:

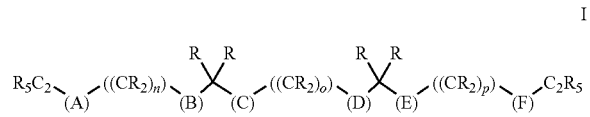

wherein, at least one of A, B, C, D, E and F is selected from the group consisting of:

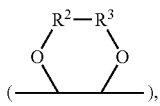

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino ($C_{1-26}$)alkyl, amino($C_{6-10}$)aryl, heteroaryl, $C_{3-6}$ cycloalkyl and phenyl($C_{1-26}$)alkyl;

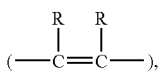

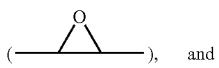

the other of A, B, C, D, E and F is independently selected from the group consisting of: i, ii, iii, iv and v;

R is in each instance independently selected from the group consisting of:

hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl;

n is an integer between about 1 and about 6;
o is an integer between about 10 and about 20; and
p is an integer between about 1 and about 6,
provided that,
if C and D are both

o is 14 or 22, and every instance of R is hydrogen, then at least one of A, B, E and F is other than $CH_2$.

Long-chain hydrocarbons can be prepared by electrochemical coupling of unsaturated fatty acids. Fatty acids subjected to a current density under the conditions described herein can oxidize and decarboxylate. The decarboxylated fatty acid forms a hydrocarbon radical capable of combining with another hydrocarbon radical. When two unsaturated hydrocarbon radicals couple, a compound of Formula I is formed. The compound can be a symmetrical compound as represented by structures 1 and 9. However, if a mixture of fatty acids is present in the reaction, a mixture of coupled products will be obtained. Two radicals each having a different chain length and number of double bonds can combine to form cross-coupling reaction products such as those depicted in structures 2-8 above.

When the carbon chain radicals undergo coupling, several byproducts can form. Such byproducts lower the yield and current efficiency of the reaction. These competing reactions include the following:

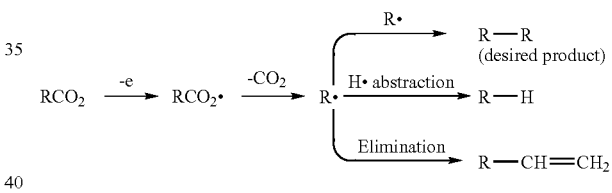

As an example of a cross-coupling reaction, a mixture of two different fatty acids will give three products in a 1:2:1 ratio:

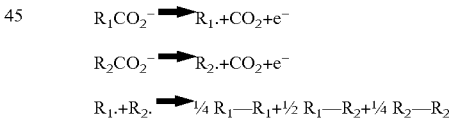

Suitable starting materials for the coupling reaction include any $C_{12-26}$ fatty acid material. Preferably, the fatty acid material contains at least two chemically different $C_{12-26}$ fatty acid residues. Purified or homogenous starting materials containing substantially one $C_{12-26}$ fatty acid residue increase the cost of producing long-chain hydrocarbons. For large-scale production of useful polyunsaturated $C_{22-50}$ hydrocarbons, and derivatives thereof, a method utilizing less costly starting materials is needed. Less refined or recycled fatty acid feedstocks are available. Other sources of fatty acids include polymerized (heat-bodied) oils, and blown oils. Polymerized oils and blown oils are known in the art. A definition for these terms of art is given in *Oils For Organic Coatings*, Federation Series on Coatings Technology, Unit Three, 1965.

A suitable starting material is the fatty acid derivatives derived from a polymerized oil. In this aspect, the fatty acid residues have been cross-linked with one or more other fatty acid residues. In each cross-linkage, the residues are attached through a carbon-carbon bond involving a chain carbon on each residue. The cross-linked fatty acids can be derived by any means known in the art for splitting a polymerized oil. A preferred method is steam splitting of the oil by mixing the oil with water and heating the mixture. This method is well-known in the art. The cross-linked fatty acids derived from the splitting can be subjected to electrocoupling as described to form useful end-products or intermediates in the production of end-products.

It has been found that soapstock is a suitable starting material for the preparation the compounds of Formula I. A soapstock may also be referred to as a Refinery Byproduct Lipid (RFB). The soapstock can also be a degummed RFB. One advantage of the present invention is the relatively low cost of soapstock. Further, soapstock is a renewable source of long-chain fatty acids. In a most preferred embodiment, the starting material is a soapstock that is subjected to electrolysis wherein a compound of Formula I is prepared. When the starting material is a soapstock, the electrocoupling process will yield one or more compounds of Formula I, without provisions:

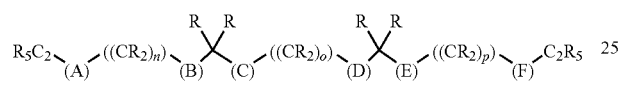

wherein, at least one of A, B, C, D, E and F is selected from the group consisting of:

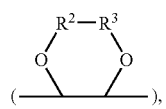

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl;

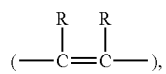

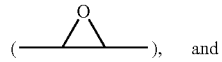, and

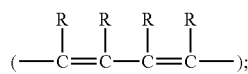

the other of A, B, C, D, E and F is independently selected from the group consisting of: i, ii, iii, iv and v;

R is in each instance independently selected from the group consisting of:

hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl;

n is an integer between about 1 and about 6;

o is an integer between about 10 and about 20; and p is an integer between about 1 and about 6.

The process can also include additional steps of derivatizing the polyunsaturated long chain hydrocarbon to form a compound of Formula I. Thus, the process can further comprise one or more of the following: epoxidation of double bonds as shown in structures provided herein; formation of embedded dioxanone rings as shown in structures provided herein; and substitution of one or more R groups as described herein. Methods of epoxidation, dioxanone ring formation and substitution at the R positions on an alkyl chain are well known in the art.

An epoxide containing derivative can be converted to yield a dioxanone ring containing derivative by methods known in the art. Under reaction conditions, there may be full or partial conversion of available epoxide residues to dioxanone residues. Furthermore, an epoxide moiety can be derivatized to the following structure during the dioxanone ring formation reaction when using ethyl lactate.

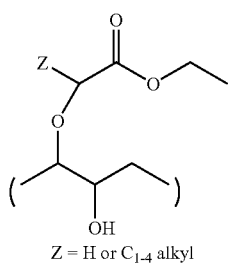

Z = H or $C_{1-4}$ alkyl

Other suitable starting materials containing $C_{12}$-$C_{26}$ fatty acids include acid oils or feedstocks derived by splitting or saponification of esters such as fatty acid methyl esters or acyglycerols. Waste frying oils from restaurants are suitable examples of the latter feedstock. Wood oils such as tung oils, and animal-derived oils, such as tallow or lanolin are also suitable starting materials. The fatty acid starting material can be a vegetable oil fatty acid material. Vegetable oil fatty acids are derived from vegetable oils. Preferred vegetable oils include, but are not limited to, soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives, conjugated derivatives, genetically-modified derivatives and mixtures thereof. As used herein, a reference to a vegetable oil includes all its derivatives as outlined above. Conjugated fatty acids, such as those formed by hydrogenation, deodorization or heat-treatment of polyunsaturated oils or fatty acids are suitable feedstocks. For instance, the use of the term "linseed oil" includes all derivatives including conjugated linseed oil.

Fatty acids derived from vegetable oils include fatty acids containing carbon chains of about 12 to about 26 carbons. More preferably, the carbon chain contains about 14 to about 24 carbons. Most preferably, the number of carbons is about 16 to about 20. Preferably, the fatty acid is unsaturated. Preferred fatty acids include, but are not limited to, palmitoleic acid, oleic acid, linoleic acid, linolenic acid, eleostearic acid, ricinoleic acid, arachidonic acid, cetoleic acid, eicosapentaenoic acid, docosahexaenoic acid or erucic acid.

When the fatty acid starting material is other than a soapstock, it is preferred that the fatty acids in the starting material are first converted to a soap. As an example, fatty acids can be combined with sodium methoxide to form carboxylate salts. Methods of preparing carboxylate salts (soap) are well known in the art.

The fatty acid material is subjected to a current supplied by any means capable of delivering a current potential. A preferred method of delivering a current potential is through the use of a potentiostat/galvanostat capable of maintaining a current between two electrodes. A reaction vessel containing the electrodes, and a stirring or mixing apparatus is preferred. Preferably, the fatty acid material is dissolved in a suitable solvent such as methanol, stirred in a reaction vessel and subjected to an electric current while stirring. Solvents can be any polar protic solvent such as a low weight alcohol, preferably methanol or ethanol. Polar aprotic solvents are also suitable, including N,N-dimethylformamide. The reaction vessel can be water-jacketed to help regulate temperature.

The current density and temperature of the reaction can be optimized for a particular type of fatty acid or mixtures of fatty acids. The temperature of the reaction can be affected by the solvent used. Preferably, the reaction temperature is between about 10° C. and about 100° C. More preferably, the temperature is between about 20° C. and about 60° C. Current density, I, is measured in amperes per cm$^2$ (A cm$^{-2}$). Useful values for current density range from about 0.1 to about 0.7 when the temperature is between about 40° C. and 60° C. The yield of the reaction can depend on the temperature and current density. The current efficiency of the reaction is reported herein to show the relationship between current density and temperature. However, some coupling reactions are not dependent on these variables. This finding is only a qualitative characteristic and does not significantly affect the quantitative yield as the examples provided herein demonstrate. It would not require undue experimentation to determine optimal reaction conditions since it has now been shown that the coupling reaction proceeds in the presence of long-chain hydrocarbons that contain at least one site of unsaturation.

Another advantage of the present method is that byproducts that are often produced can also be useful products. For example, fatty acid alkyl esters of Formula II below can be produced during electrolysis of long chain fatty acids. Such alkyl esters, especially methyl esters, can be used, among other things, as biodiesel. Terminal olefins of Formula III below can also be formed during the present method. The alkyl esters and terminal olefins can be separated from one another and a compound of Formula I by various distillation techniques known in the art. On the other hand, a composition comprising a compound of Formula I may also contain such byproducts formed during electrolysis. In the case of alkyl esters and terminal olefins, these chemicals can modify the physical, rheologic and chemical characteristics of the composition.

The present invention is further directed to a method of preparing compounds of Formula II:

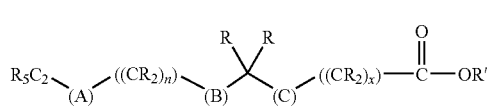

wherein,
at least one of A, B and C is selected from the group consisting of:

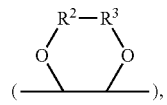

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl;

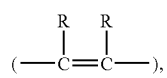

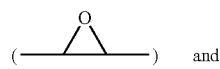 and

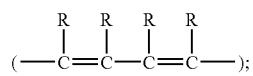

the other of A, B and C is independently selected from the group consisting of: i, ii, iii, iv and v;

R is in each instance independently selected from the group consisting of: hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl;

x is an integer between about 5 and about 10; more preferably x is about 7; n is an integer between about 1 and about 6; more preferably n is between about 1 and about 3 if A is CR$_2$; if A is —C═C—, then preferably n is about 1;

R' is a $C_{1-4}$ alkyl;

the method comprising, (a) subjecting a $C_{12-26}$ fatty acid material containing at least two chemically different $C_{12-26}$ fatty acid residues to an electric current in a solvent selected from an alcohol having the formula R'—OH, wherein a compound of Formula II is prepared. The particular alcohol used will yield specific alkyl esters. For instance, when R' is methyl, the alkyl ester produced is a methyl ester. Preferred $C_{1-4}$ alcohols include methanol and ethanol. Most preferably, the alcohol is methanol. The starting materials for this method are the same as described above for the preparation of compounds of Formula I. The conditions for preparing a compound of Formula II are as described above for Formula I.

The process can also include additional steps of derivatizing the polyunsaturated long chain hydrocarbon to form a compound of Formula II. Thus, the process can further comprise one or more of the following: epoxidation of double bonds as shown in structures provided herein; formation of embedded dioxanone rings as shown in structures provided herein; and substitution of one or more R groups as described herein. Methods of epoxidation, dioxanone ring formation and substitution at the R positions on an alkyl chain are well known in the art.

The present invention is directed to a method of preparing compounds of Formula III:

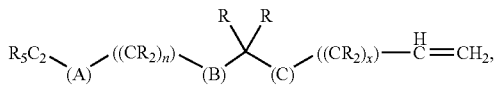

wherein,
at least one of A, B and C is selected from the group consisting of:

ii

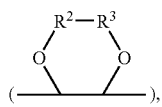

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino ($C_{1-26}$)alkyl, amino($C_{6-10}$)aryl, heteroaryl, $C_{3-6}$ cycloalkyl and phenyl($C_{1-26}$)alkyl;

iii

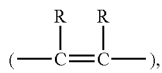

iv

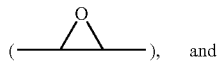   and v

the other of A, B and C is independently selected from the group consisting of: i, ii, iii, iv and v;
R is in each instance independently selected from the group consisting of: hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino ($C_{1-26}$)alkyl, amino($C_{6-10}$)aryl, heteroaryl, $C_{3-6}$ cycloalkyl and phenyl($C_{1-26}$)alkyl;
x is an integer between about 5 and about 10; more preferably x is about 5; n is an integer between about 1 and about 6; more preferably n is between about 1 and about 3 if A is $CR_2$; if A is —C═C—, then
preferably n is about 1;

the method comprising, (a) subjecting a $C_{12-26}$ fatty acid material containing at least two chemically different $C_{12-26}$ fatty acid residues to an electric current, wherein a compound of Formula III is prepared. The terminal double bond can either be a cis or trans configuration. The starting materials for this method are the same as described above for the preparation of compounds of Formula I. The conditions for preparing a compound of Formula III are as described above for Formula I.

The process can also include additional steps of derivatizing the polyunsaturated long chain hydrocarbon to form a compound of Formula III. Thus, the process can further comprise one or more of the following: epoxidation of double bonds as shown in structures provided herein; formation of embedded dioxanone rings as shown in structures provided herein; and substitution of one or more R groups as described herein. Methods of epoxidation, dioxanone ring formation and substitution at the R positions on an alkyl chain are well known in the art.

The present invention is also directed to compositions comprising a compound of Formula I. Preferred compositions include epoxy formulations, thermoset plastics, PVC polymers and coating compositions such as paint. The preferred compositions will comprise a compound of Formula I and a latex polymer, PVC, epoxy resin or alkyd resin for example. The compositions can further comprise additives, surfactants, pigments, modifiers and the like.

Any latex resin suitable as a component in a coating composition can be used in the present invention. Such latex resins are commercially available and well known in the art. Suitable latex resins include, but are not limited to, styrene-acrylic, styrenics, vinyl-acrylic, styrene-butadiene, vinyl acetate, vinyl versatate and the like.

In coating compositions, a compound of Formula I can be present in any amount that results in a final coating composition having the desired rheologic properties such as pour point and viscosity. Alternatively, a compound of Formula I can be added to a composition as a reactive diluent. In this embodiment, the compound contains one of the following: one or more double bonds, one or more dioxanone ring systems embedded in the carbon chain, one or more oxirane ring systems embedded in the carbon chain, or the carbon chain is optionally substituted to provide chemical reactivity. When a double bond is present in the molecule, the double bond is a site for oxidative curing and crosslinking. When the compound contains an oxirane ring, the ring is a site for urethane formation when an appropriate amine is also provided in the composition. The epoxide moiety can also scavenge HCl formed during the decomposition of PVC polymers. Thus, an epoxidized compound of Formula I can also be used as a stabilizer in certain polymer compositions. When the compound contains a dioxanone ring, the ring is a site for urethane formation when an appropriate amine is also provided in the composition. The compound can further contain substitutions at the R positions which give the compound the desired rheologic properties in its end use as described herein.

A composition can contain one or more compounds of Formula I. A thermoset plastic composition can comprise an epoxy resin composition as described herein and an amine. The amine functionality can be provided by a compound of Formula I or can be added as a separate component as listed below. Further, in an epoxy or paint composition, a compound of Formula I can also provide a double bond, oxirane or dioxanone ring system that can react with the amine described above. The one or more oxirane or dioxanone rings contained in the carbon chain portion of the compound can react with an amine to form a urethane. Any amine capable of combining with an oxirane to form a urethane linkage is a suitable amine. Preferably, the amine is a diamine or triamine that is capable of reacting with multiple oxirane moieties thereby creating a crosslinked urethane thermoset plastic upon curing. Preferred amines include aliphatic and aromatic amines which may or may not contain two or more primary or secondary amines. Another preferred amine is a compound of Formula I wherein at least one R is an amine capable of forming a urethane. Additional examples include, but are not limited to, ethylene diamine, methylene dianiline diethylene triamine, polyamides, imidazoles and anhydrides such as pyromellitic acid dianhydride.

The amount of compound present will vary according to the specific type of polymer or resin blended with the compound. In many useful compositions the amount of compound relative to the polymer or resin will not exceed 70 percent by weight of the polymer or resin. Preferably, the compound is present in an amount between about 1 percent and about 70 percent by weight of the polymer or resin. More preferably, the compound is present in an amount between about 5 percent and about 40 percent. Most preferably, the compound is present in an amount between about 10 percent and about 20 percent.

The present invention is also directed to a method of preparing a composition comprising combining a polymer or resin and a compound of Formula I.

Any epoxy resin suitable as a component in an epoxy resin composition can be used in the present invention. Such epoxy resins are commercially available and well known in the art. Suitable epoxy resins include, but are not limited to, Bisphenol A and F, Novolac, epoxy acrylate, epoxy vinyl ester resins, glycol epoxy and brominated epoxy resins.

The present invention is also directed to a method of preparing a thermoset plastic comprising combining: (a) an epoxy resin comprising a compound of Formula I, wherein the compound has at least one oxirane or dioxanone ring formed between two adjacent carbons in the carbon chain, and (b) an amine. Preferably, the amine is a diamine or triamine that is capable of reacting with multiple oxirane or dioxanone moieties thereby creating a crosslinked urethane thermoset plastic upon curing. Any amine capable of combining with an oxirane to form a urethane linkage is a suitable amine. Preferred amines include those listed above.

In another aspect, the present invention is directed to a polymer composition comprising polyvinyl chloride (PVC) and a compound of Formula I, wherein the compound has at least one oxirane ring formed between two adjacent carbons in the carbon chain of the fatty acid. In this embodiment, the compound of Formula I can act as a scavenger by neutralizing HCl formed by the decomposition of the PVC polymer.

When a compound of Formula I contains a double bond, the double bond can be subjected to ozonolysis. Ozonolysis of double bonds is well known in the art. Ozonolysis cleaves the double bonds and oxidizes each carbon of the double bond to a carboxylic acid. As can be seen from the representative structures 9 and 10 above, ozonolysis can also yield dicarboxylic acids containing 16 carbons. Thus, ozonolysis of a compound of Formula I is a method of producing varying-length carboxylic acids and di-carboxylic acids preferably from a soapstock starting material.

The term "alkyl" as employed herein by itself or as part of another group refers to both straight and branched chain radicals of up to 26 carbons, preferably 6 carbons, more preferably 4 carbons, such as methyl, ethyl, propyl, isopropyl, butyl, t-butyl, and isobutyl.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 26 carbon atoms in length.

The term "aryl" as used herein by itself or as part of another group refers to monocyclic or bicyclic aromatic groups containing from 6 to 12 carbons in the ring portion, preferably 6-10 carbons in the ring portion, such as the carbocyclic groups phenyl, naphthyl or tetrahydronaphthyl. The term "aryl" can represent carbocyclic aryl groups, such as phenyl, naphthyl or tetrahydronaphthyl, as well as heterocyclic aryl ("heteroaryl") groups, such as pyridyl, pyrimidinyl, pyridazinyl, furyl, and pyranyl.

The term "heteroaryl" as used herein refers to groups having 5 to 14 ring atoms; 6, 10 or 14 π-electrons shared in a cyclic array; and containing carbon atoms and 1, 2 or 3 oxygen, nitrogen or sulfur heteroatoms. Examples of heteroaryl groups include thienyl, imadizolyl, oxadiazolyl, isoxazolyl, triazolyl, pyridyl, pyrimidinyl, pyridazinyl, furyl, pyranyl, thianthrenyl, pyrazolyl, pyrazinyl, indolizinyl, isoindolyl, isobenzofuranyl, benzoxazolyl, xanthenyl, 2H-pyrrolyl, pyrrolyl, 3H-indolyl, indolyl, indazolyl, purinyl, 4H-quinolizinyl, isoquinolyl, quinolyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, and phenoxazinyl groups. Especially preferred heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

The term "cycloalkyl" as used herein by itself or as part of another group refers to cycloalkyl groups containing 3 to 9 carbon atoms, more preferably, 3 to 8 carbon atoms. Typical examples are cyclopropyl, cyclobutyl, cyclopentyl, cyclohexyl, cycloheptyl, cyclooctyl and cyclononyl.

The term "phenyl($C_{1-26}$)alkyl" as used herein refers to $C_{1-26}$ alkyl groups as referred to above having a phenyl substituent and includes benzyl.

The term "carboxy" as used herein describes a carbon double bonded to an oxygen. The carbon may be additionally substituted.

The term "carboxyallylic" as used herein describes a carbon double bonded to an oxygen wherein the carbon is further substituted with an allylic group.

The term "carboxy($C_{1-26}$)alkyl" as used herein describes a carbon double bonded to an oxygen wherein the carbon is further substituted with a $C_{1-26}$ alkyl group.

As used herein, the terms "branched or straight chain aliphatic alcohols (hydroxy($C_{1-26}$)alkyl) and aliphatic amines (amino($C_{1-26}$)alkyl)" refer to non-aromatic hydrocarbon chains that contain an —OH or —$NR_2$ group. The R group in each instance is independently hydrogen or $C_{1-26}$ alkyl. More preferably, both R groups are hydrogen.

It is understood that the present invention encompasses the use of stereoisomers, diastereomers and optical isomers.

When any variable occurs more than one time in any constituent its definition on each occurrence is independent of its definition at every other occurrence. Also, combinations of substituents and/or variables are permissible only if such combinations result in stable compounds. Stable compounds refer to those compounds that can retain chemical reactivity, but do not spontaneously decompose by intramolecular reactions under the conditions used for their preparation.

This disclosure describes compounds of Formula I and the uses thereof. The compounds can be used, among other things, as coalescing aids and reactive diluents in latex or alkyd paints and epoxy resin formulations and as plasticizers for polymers. The functions of the compounds of Formula I in compositions described herein are not limited to the functions explicitly described.

The following schemes depict a synthetic route for preparing compounds of Formula I and derivatives thereof.

Scheme 1 depicts the decarboxylation of 2 linoleic acids and the coupling of 2 linoleic acid radicals.

SCHEME 1

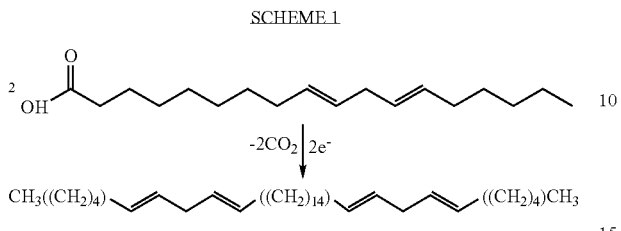

Scheme 2 depicts a synthetic route for preparing an epoxidized derivative of a compound of Formula I. In this example, the derivative is fully epoxidized. However, epoxidized derivatives comprise derivatives which may be only partially epoxidized and therefore may contain double bonds. The C=C bonds in the carbon chain can be epoxidized using an oxidant such as hydrogen peroxide. The chemical pathway usually employs formic acid or the combination of acetic acid and a strong mineral acid. Enzymes capable of facilitating epoxidation include lipase from *Candida antartica* such as Novozyme 435 (Novozymes). (Klass, M. R. and Warwel, S. "Chapter 10. New Oxidation Methods for Unsaturated Fatty Acids, Esters and Triglycerides." in Recent Developments in the Synthesis of Fatty Acid Derivatives, G. Knothe and J. Derksen, eds. AOCS Press, Champaign Ill., 1999.) If lipase is used, the process has the potential to operate in a one-pot synthesis.

SCHEME 2

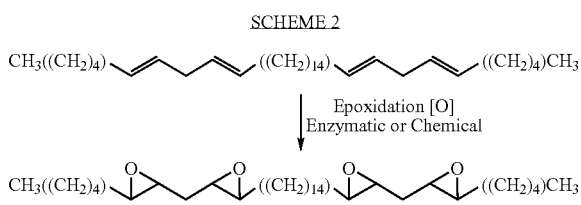

Scheme 3 depicts a synthetic route for preparing a dioxanone derivative of a compound of Formula I. In this specific example, several epoxide rings remain intact.

SCHEME 3

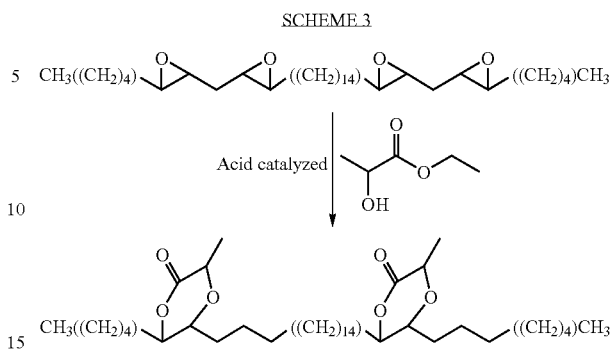

EXAMPLES

Example 1

Electrocoupling of Long-chain Fatty Acids

About 3.0 to about 4.0 mmol of fatty acid was dissolved in methanol, followed by neutralization with about 0.3 to about 0.6 mL of 1M sodium methoxide. A potentiostat/galvanostat with a 100-V maximum compliance voltage (Princeton Applied Research Model 173) maintained a constant current between the platinum electrodes (1.5 cm×1.5 cm and 2.5 cm×1.0 cm, spaced <0.5 cm apart). The electrolysis was carried out in a water-jacketed cell to maintain a constant temperature, which is generally set at a temperature between about 40° C. and about 60° C. A magnetic stir bar was used to agitate the reaction mixture. When an electrical charge equivalent to 1.3 Faradays per mole of the starting acid at the specified current density (generally between 0.05 and 0.12 A $cm^{-2}$, or about 0.18-0.63 A) passed through the reaction mixture, the electrolysis was halted. The reaction mixture was acidified with a few drops of concentrated HCl, the addition of which converted methoxide to methanol and protonated carboxylate ions. Following evaporation of methanol, the crude product was dissolved in 50 mL of hexanes, transferred to a 125 mL separatory funnel, and washed with three 75 mL volumes of water at 60° C.

Table 1 shows the coupling product obtained from corresponding fatty acids.

| Fatty Acid (Starting Material) | Coupling Product |
|---|---|
| $CH_3(CH_2)_4COOH$ | $CH_3(CH_2)_8CH_3$ |
| Hexanoic Acid | n-decane |
| $CH_3(CH_2)_6COOH$ | $CH_3(CH_2)_{12}CH_3$ |
| Octanoic Acid | n-tetradecane |
| $CH_3(CH_2)_{14}COOH$ | $CH_3(CH_2)_{28}CH_3$ |
| Palmitic Acid | (11) n-triacontane |
| $CH_3(CH_2)_{16}COOH$ | $CH_3(CH_2)_{32}CH_3$ |
| Stearic Acid | (12) n-tetratriacontane |
| $CH_3(CH_2)_7CH=CH(CH_2)_7COOH$ | $CH_3(CH_2)_7CH=CH(CH_2)_{14}CH=CH(CH_2)_7CH_3$ |
| Oleic Acid | (10) 9,25-tetratriacontadiene |
| $CH_3(CH_2)_4(CH=CHCH_2)_3(CH_2)_6COOH$ | $CH_3(CH_2)_4(CH=CHCH_2)_2(CH_2)_{12}(CH_2CH=CH)_2(CH_2)_4CH_3$ |
| Linoleic Acid | (1) 6,9,25,28-tetratriacontatetraene |
| $CH_3(CH_2)(CH=CHCH_2)_3(CH_2)_6COOH$ | $CH_3(CH_2)(CH=CHCH_2)_3(CH_2)_{12}(CH_2CH=CH)_3CH_2CH_3$ |
| Linoleic Acid (Linseed Oil) | (7) 3,6,9,25,28,31-tetratriacontahexaene |

Example 2

Synthesis of n-triacontane (11)

Compound 11 was synthesized according to the method of Example 1. Table 2 summarizes the yield and current efficiency for the conversion of palmitic (3) to n-triacontane. Yields are reproducible. The maximum yield (88%) was obtained at 60° C. and 0.45 A cm$^{-2}$, and 40° C. and 0.23 A cm$^2$.

| T (° C.) | I (A cm$^{-2}$) | Yield of 11 (%) | Current Efficiency (%) |
| --- | --- | --- | --- |
| 40 | 0.23 | 88.3 ± 4.7 | 67.8 ± 3.6 |
| 40 | 0.36 | 83.5 ± 11.1 | 64.6 ± 8.6 |
| 40 | 0.45 | 83.8 ± 5.7 | 66.7 ± 5.7 |
| 40 | 0.54 | 79.4 ± 2.5 | 61.5 ± 1.9 |
| 40 | 0.45 | 83.8 ± 7.1 | 66.7 ± 5.7 |
| 50 | 0.45 | 61.6 ± 22.2 | 49.1 ± 17.7 |
| 60 | 0.45 | 88.5 ± 1.6 | 70.5 ± 1.3 |

Example 3

Synthesis of n-tetratriacontane (12)

Compound 12 was synthesized according to the method of Example 1. Table 3 summarizes the yield and current efficiency for the conversion of stearic acid (4) to n-tetratriacontante. The yields are lower than those obtained for the preparation of (11) above. The maximum yield (~50%) was obtained under the following conditions: at 60° C. and 0.45 A cm$^{-2}$, and 40° C. and 0.23 A cm$^{-2}$.

| T (° C.) | I (A cm$^{-2}$) | Yield of 12 (%) | Current Efficiency (%) |
| --- | --- | --- | --- |
| 40 | 0.23 | 48.6 ± 4.0 | 38.0 ± 3.1 |
| 40 | 0.36 | 46.1 ± 3.3 | 26.2 ± 2.6 |
| 40 | 0.45 | 37.5 ± 0.9 | 29.4 ± 0.7 |
| 40 | 0.54 | 42.7 ± 6.3 | 33.1 ± 4.9 |
| 40 | 0.45 | 37.5 ± 0.9 | 29.4 ± 0.7 |
| 50 | 0.45 | 37.6 ± 1.2 | 29.5 ± 0.9 |
| 60 | 0.45 | 50.2 ± 9.9 | 39.5 ± 7.8 |

Example 4

Synthesis of 9,25-tetratriacontadiene (10)

Compound 10 was synthesized according to the method of Example 1. Table 4 summarizes the yield and current efficiency for the conversion of oleic acid (5) to 9,25-tetratriacontadiene. The yield for this reaction is >90%.

| T (° C.) | I (A cm$^{-2}$) | Yield of 10 (%) | Current Efficiency (%) |
| --- | --- | --- | --- |
| 40 | 0.23 | 92.7 ± 3.0 | 73.2 ± 2.2 |
| 40 | 0.36 | 96.7 ± 1.3 | 74.8 ± 0.9 |
| 40 | 0.45 | 95.3 ± 1.5 | 73.3 ± 1.1 |
| 40 | 0.63 | 97.4 ± 0.4 | 76.3 ± 0.3 |

Example 5

Synthesis of 6,9,25,28-tetratriacontatetrane (1)

Compound 1 was synthesized according to the method of Example 1. Table 5 summarizes the yield and current efficiency for the conversion of linoleic acid (6) to 6,9,25,28-tetratriacontatetrane. The maximum yield for this reaction is 19% at 0.23 A cm$^{-2}$.

| T (° C.) | I (A cm$^{-2}$) | Yield of 1 (%) | Current Efficiency (%) |
| --- | --- | --- | --- |
| 40 | 0.23 | 19.1 ± 3.0 | 14.7 ± 2.3 |
| 40 | 0.36 | 12.8 ± 1.6 | 9.95 ± 1.27 |
| 40 | 0.45 | 5.64 ± 0.9 | 4.36 ± 4.36 |
| 40 | 0.54 | 8.61 ± 2.8 | 6.77 ± 2.19 |

Example 6

Synthesis of 3,6,9,25,28,31-tetratriacontahexaene (7)

Compound 7 was synthesized according to the method of Example 1. Linseed oil (57% linolenic acid, 14% linoleic acid, 19% oleic acid, 0.5% palmitoleic acid, 3.5% stearic acid and 6% palmitic acid) was subjected to electrocoupling. Gas chromatography indicated that several coupling and cross-coupling products formed. As a result of the amount of linolenic, linoleic and oleic acid present in the starting oil, coupling of linolenic acid likely represents the major product. Other significant products indicated by gas chromatography include cross-coupling of linolenic with linoleic and oleic acids.

Example 7

Relative Concentrations of Byproducts

The following data represent estimates of the relative concentrations of methyl esters and terminal alkene/alkane produced during coupling of homogenous acids.

| Palmitic Acid | |
| --- | --- |
| Methyl ester | 5-28% |
| Terminal alkene/alkane | 4-8% |
| Stearic Acid | |
| Methyl ester | 45-65% |
| Terminal alkene/alkane | 3-5% |
| Oleic Acid | |
| Methyl ester | 2-11% |
| Terminal alkene/alkane | 1-5% |

-continued

| Linoleic Acid | |
|---|---|
| Methyl ester | 70-83% |
| Terminal alkene/alkane | 10-15% |

Example 8

Use of Dimethylformamide as a Solvent for Electrocoupling

The coupling of palmitic acid was carried out in dimethylformamide (DMF) and in ethanol according to the method of example 1. Analysis indicated that the formation of methyl esters did not occur.

| Solvent | Max. Current, (A cm$^3$) | Time (seconds) | Charge (C) | Yield (%) |
|---|---|---|---|---|
| Methanol | 0.12 | 1800 | 972 | 75 |
| Ethanol | 0.03 | 7200 | 936 | 78 |
| Dimethylformamide | 0.02 | 9000 | 810 | 75 |

Example 9

Electrocoupling of Linseed Oil

The electrocoupling of linseed oil was carried out according to the method of example 1. Linseed oil contains the following major fatty acids:

| Fatty acid in linseed oil | Content (%) |
|---|---|
| Linolenic acid | 57 |
| Linoleic acid | 14 |
| Oleic acid | 19 |
| Stearic acid | 3.5 |
| Palmitoleic acid | 0.5 |
| Palmitic acid | 6 |

Analysis of the reaction products by gas chromatography and mass spectra indicates that ten coupling products formed include:
Palmitic acid: palmitic acid
Palmitic acid: linoleic acid
Palmitic acid: oleic acid
Linolenic acid: linolenic acid
Stearic acid: stearic acid Example 10

Electrocoupling of Fatty Acid Derivatives Obtained from Heat-Polymerized Oil

The electrocoupling of fatty acids from heat-polymerized linseed oil (OKO M2 ½, obtained from Archer Daniels Midland, Decatur, Ill.) was carried out according to the method of example 1. The triglyceride heat-polymerized linseed oil was split into fatty acid derivatives by mixing with an equal quantity of water followed by steam splitting in batch mode at 230° C. for 3 hours by methods well-known in the art. A solid fatty acid mixture was obtained. After the fatty acid mixture was subjected to electrocoupling according to the method of example 1, a liquid product was obtained.

Having now fully described this invention, it will be understood to those of ordinary skill in the art that the same can be performed within a wide and equivalent range of conditions, formulations, and other parameters without affecting the scope of the invention or any embodiment thereof.

What is claimed is:

1. A compound of formula I:

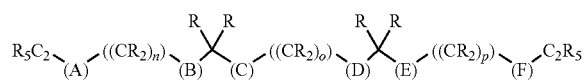

wherein

A, B, C, D, E and F are each independently selected from the group consisting of:

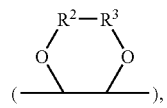

wherein, one of $R^2$ and $R^3$ is a carbonyl and the other of $R^2$ and $R^3$ is $CR_4R_5$, and wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, $C_{3-6}$ cycloalkyl and phenyl($C_{1-26}$)alkyl;

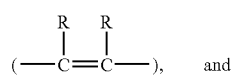

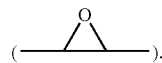

R is in each instance independently selected from the group consisting of:
hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)heteroaryl, $C_{3-6}$ cycloalkyl and phenyl ($C_{1-26}$)alkyl;
n is an integer between about 1 and about 6;
o is an integer between about 10 and about 20; and
p is an integer between about 1 and about 6.

2. The compound of claim 1, wherein
n is 1,
p is 1, and
o is 14.

3. The compound of claim 2, wherein
at least one R is a $C_{1-26}$ alkyl, hydroxy($C_{1-26}$)alkyl or amino ($C_{1-26}$)alkyl, and other instances of R are hydrogen.

4. The compound of claim 1, wherein at least one of A, B, C, D, E and F is

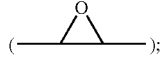 iv and the other of A, B, C, D, E and F are

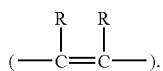 iii

5. The compound of claim 4, wherein at least one R is a $C_{1-26}$ alkyl, hydroxy($C_{1-26}$)alkyl or amino ($C_{1-26}$)alkyl, and other instances of R are hydrogen.

6. The compound of claim 1, wherein
at Least one of A, B, C, D, E and F are

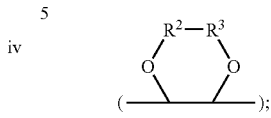 ii and the other of A, B, C, D, B and F are

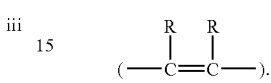 iii

7. The compound of claim 6, wherein
n and p are each 1, and
o is 14.

8. The compound of claim 7 wherein,
at least one R is a $C_{1-26}$ alkyl, hydroxy($C_{1-26}$)alkyl or amino ($C_{1-26}$)alkyl, and other instances of R are hydrogen.

* * * * *

UNITED STATES PATENT AND TRADEMARK OFFICE
CERTIFICATE OF CORRECTION

PATENT NO. : 7,582,777 B2  Page 1 of 1
APPLICATION NO. : 11/250622
DATED : September 1, 2009
INVENTOR(S) : Bloom It is certified that error appears in the above-identified patent and that said Letters Patent is hereby corrected as shown below:

Title Page,

[*] Notice: Subject to any disclaimer, the term of this patent is extended or adjusted under 35 USC 154(b) by (545) days Delete the phrase "by 545 days" and insert -- by 864 days --

Signed and Sealed this

Twentieth Day of July, 2010

David J. Kappos
*Director of the United States Patent and Trademark Office*